US005798096A

United States Patent [19]

Pavlyk

[11] Patent Number: 5,798,096
[45] Date of Patent: Aug. 25, 1998

[54] BIOCOMPATIBLE HYDROGEL

[75] Inventor: Boris Ivanovich Pavlyk, Kiev, Ukraine

[73] Assignee: Maloe Vnedrencheskoe Predpriyatie "Interfall", Kiev, Ukraine

[21] Appl. No.: 776,731

[22] PCT Filed: Aug. 12, 1994

[86] PCT No.: PCT/UA94/00022

§ 371 Date: Jan. 23, 1997

§ 102(e) Date: Jan. 23, 1997

[87] PCT Pub. No.: WO96/04943

PCT Pub. Date: Feb. 22, 1996

[30] Foreign Application Priority Data

Aug. 10, 1994 [UA] Ukraine ............... 94086726

[51] Int. Cl.⁶ ............................................. A61F 2/02
[52] U.S. Cl. ............................ 424/78.35; 424/78.31; 424/422; 424/423; 424/487; 252/315.1; 526/303.1
[58] Field of Search ............... 424/78.35, 487, 424/78.31, 422; 252/315.1; 526/303.1

[56] References Cited

U.S. PATENT DOCUMENTS

| | | | |
|---|---|---|---|
| 4,657,656 | 4/1987 | Ogawa | 204/299 R |
| 4,746,551 | 5/1988 | Allen | 427/389.7 |
| 5,135,480 | 8/1992 | Bannon | 604/20 |
| 5,244,799 | 9/1993 | Anderson | 435/240 |
| 5,306,404 | 4/1994 | Notsu | 204/182.8 |
| 5,344,451 | 9/1994 | Dayton | 23/8 |
| 5,482,719 | 1/1996 | Guillet | 424/486 |
| 5,589,104 | 12/1996 | Bambeck | 252/315.1 |

*Primary Examiner*—Fred Zitomer
*Attorney, Agent, or Firm*—Ilya Zborovsky

[57] ABSTRACT

A BIOCOMPATIBLE HYDROGEL, is provided for use in the treatment of humans for cosmetic and functional defects (e.g. in mammas, vocal cords, penis, etc. as endoprostheses), in the provision of intratissue storage sites the prolonged-action medicinal preparations, in various applications as electroconductive immersion media, and in the life-long tamponing of caverns. It contains an acrylamide-based polymer produced in the presence of an initiator of radical polymerization in apyrogenic water as the dispersion medium. An increase in elasticity, shape retention capability, and stability of bulky implants, as well as corresponding therapeutic and cosmetic efficacy, mainly in the endoprosthetic applications is achieved due to the hydrogel containing cross-linked polyacrylamide produced by using a biocompatible cross-linking agent, such as methylene-bis-acrylamide, and preferably a mixture of ammonium persulfate and tetramethylethylenediamine as the initiator of polymerzation. A preferred concentration of the novel polymer in the hydrogel is from 3.5 to 9% by mass.

1 Claim, 1 Drawing Sheet

BIOCOMPATIBLE HYDROGEL

FIELD OF INVENTION

The invention relates to formulations of biocompatible hydrogels for medical applications which can be used:

in endoprosthesis practice by way of purposeful injections to remedy preferably those defects in humans which are due to traumatic, congenital or age distorsions of the shape and dimensions or due to loss of form stability of some organs consisting of soft tissues, e.g.:

plastic surgery for correcting the form and dimensions of the face and other parts of the body and, specifically, mammoplasty (preferably in the case of mammary aplasia or hypomastia), male sexology (in the cases of feeble erection) for improving potency through injecting an elastic medium into spongy vascular tissue of the penis.

Demands for an improvement in bodily shape and functioning as mentioned above and other similar cases have become widespread and are frequently reasoned by the mere patient's desire.

That is why biocompatible materials for the above mentioned applications should satisfy some hardly consistent requirements. Among the most important requirements are:

long-term (preferably life-long) retaining of the shape and dimensions of an organ, where an endoprosthesis has been placed, irrespective of the age when the patient was operated;

minimal trauma occurance and the shortest possible introduction of a biocompatible material, especially in large-dosage (up to 1000 ml) applications.

That is why to meet the above application requirements it is practical to use gelling biocompatible materials.

Actually, minimal trauma occurance and the shortest possible introduction of a biocompatible material, absence of carcinogenicity and minimal allergic reactions being the fact, are achieved by using a water solution of bovine collagen which, being a highly refined and partially depolymerized product, turns into an elastic and mechanically stable hydrogel at a temperature below 37 deg. C. following injection into the organ that has been treated as to shape and dimensions (see (Ford Ch., Martin D. M., Warner Th. F. Injectable collagen in laryngeal rehabilitation// LARYNGOSCOPE, 1984, 94, pp.513–518).

Being protein, collagen, however, would completely be resorbed in the patient's body in a considerably short period of time (less than half a year).

It is, therefore, suitable for use in endoprosthetic practice primarily in the cases when a complete substitution of an endoprosthesis for connective tissues is acceptable or when a patient, according to medical indications, needs a precisely temporary endoprosthesis.

It should be also noted that due to its resorption ability and to intra-tissue and inter-tissue migration, and whereas it is susceptible of an enzyme attack, the bovine collagen solution is practically unsuitable for application as a material for long-term endoprostheses.

Considering the above, the gelling biocompatible materials based on synthetic polymers are more preferable.

Thus, the biocompatible gelling material in the form of hydrophilic esters of polyglycols and of metacrylic acid is known to be applied in endoprosthetic practice (Kresa L., Rems T., Wichterle O. Hydrogel implant in vocal cord// Otolaryngol. Head Neck Surg.—1988, V. 98, No 3, pp. 242–245).

A required dose of such dry material is implanted via a section in the region of cosmetic or functional treatment and then the operative wound is satured. Thereafter, the material swells by absorbing water from adjacent tissues, to thereby provide for a local increase in the volume of the corrected organ.

This biocompatible material is characterized by a high biochemical stability.

In application, however, a durable therapeutic effect is achieved at the expense of traumatic surgical interventions associated with edemas and aseptic inflammations.

Therefore, the most promising for endoprosthetic practice and other applications are commercially available injectable liquid biocompatible gelling materials.

The biocompatible gelling material as a solution containing water-insoluble polymers, among them non-cross-linked acrylonitrile polymers or their copolymers, polyvinylacetate, a linear or low-branched polymer or copolymer of 2-hydroxyethyl-acrylate and methyl-acrylate, poly-n-vinyliminocarbonile and dimethylsulfoxide or other polar readily miscible with water organic solvents, may be exemplified (Stoy V., Chvapil M., U.S. Pat. No. 4,631,188; 1986). In obtaining copolymers, use may be made of additional monomers, such as acrylamide (including N-substituted), acrylhydrazide (including N-substituted), acrylic acid and acrylates, glutarimide and vinyl sulfone; and the polar readily miscible with water solvents such as glycerol and its mono- or diacetates, methanol, ethanol, propanol and izopropanol, dimethylformamide, glycols and other suitable solvents.

This material is highly efficient in the treatment of minor cosmetic or functional defects, specifically lips and other parts of a face.

However, in correcting the mammary form and dimensions with endoprostheses, up to 1 liter of the material can be required. In such cases, an amount of an organic solvent, injected together with the gelling polymer, sustantially exceeds the physiologically permissible minimum to result in erythema and, in some cases, an allergic shock. Also, due to a linear structure of the gelling polymer applied, endoprostheses are observed to have a low form-stability, the greater in volume, the lower in quality.

That is why, the most preferable are commercially available hydrogels that contain no allergens.

Among them, the most closely bearing on the invention is a biocompatible hydrogel containing 3.0% by weight of a polymer based on acrylamide produced by the use of a free-radical polymerization initiator (specifically, ammonium persulfate) in a dispersion medium such as bidistilled pyrogen-free water (USSR Inventor's certificate 1,697,756).

This hydrogel is in fact completely biocompatible with the man's tissues and liquids in all the above aspects and, therefore, can be applied in considerable (up to 1 liter) amounts, causing no expressed negative biochemical and biological aftereffects. In the region of injection, it forms a structure readily permeable not only by water, ions, oxygen but by low-molecular metabolites as well. The hydrogel implants, are invaded at a considerably high rate (by the 5–6th month) with a young fibrous tissue of a recipient.

This hydrogel, however, has low viscosity and, therefore, low elasticity and high mobility. Water contained in the hydrogel is loosely bound with the macromolecules of polyacrylamide and is readily removed from the implants to result in manifest shrinkage thereof and a considerable decrease in cosmetic or teurapeutic effect. That is why, in the case of placing voluminous (e.g., intramammar) endoprostheses, the implants show as low resistance to external deformation loads and shrinkage as large is their initial volume.

Due to its high fluidity, this hydrogel has low efficiency.

Therefore, the invention has for its object to provide a biocompatible hydrogel which, by improving the polyacrylamide composition, would ensure elasticity, shape retention, and stability of bulky implants and offer greater therapeutic and cosmetic results in endoprosthetic applications.

The above problem has been resolved by providing a biocompatible hydrogel containing a polymer based on acrylamide produced by using an initiator of radical polymerization in pyrogen-free water as a dispersion medium, in which according to the invention said polymer is cross-linked polyacrylamide produced by using a biocompatible cross-linking agent.

Being permeable for water, ions, oxygen and low-molecular metabolites and being suitable for applications by injection, the hydrogel of the invention has a more regular and more advantageous water-binding structure to thereby provide for bulky, highly elastic and form-retaining implants (e.g., intramammary endoprostheses and supporting rods in the spongy vascular tissue of the penis tampons in lung caverns) that are invaded with a soft highly-vascularized connective tissue at an extremely slow rate (months to years). Due to structural, biochemical, anatomical and physiological advantages, as described above, there is a substantional cosmetic and/or therapeutic effect as well as an encrease in durability of such effects in endoprosthetic applications.

According to the first further caracterizing feature of the invention the biocompatible hydrogel contains cross-linked polyacrylamide produced by using methylene-bis-acrylamide, as a cross-linking agent, and a mixture of ammonium persulphate and tetramethylenediamine as an initiator of polymerization. Methylene-bis-acrylamide is ananalogous to the base monomer (acrylamide) both by its composition and biocompatibility, while use of the above-mentioned mixture of polymerization initiators is favorable in the fairly regular cross-linking of polyacrylamide chain macromolecules to provide an elastic space network suitable for injecting the hydrogel.

According to a further aspect of the invention the biocompatible hydrogel contains from 3.5 to 9.0% by weight of said cross-linked polyacrylamide. This range of concentration is providing the maximum therapeutic or cosmetic effect in the injection endoprosthetic practice or tamponing. Concentrations below 3.5% make the hydrogel unstable only to be applied as a base for medicinal ointments or electroconducting immersion media for cardio- or encephalography, while concentrations above 6.0% decrease fluidity of the hydrogel practically to zero and is practicable, in manufacturing relatively firm, form-retaining, precast endoprostheses that require a surgical procedure to have access to the region of placing such an endoprosthesis.

The invention is hereafter disclosed by:

a description of the initial reagents, method of preparing the novel biocompatible hydrogel, examples of carrying out the method, and the results of laboratory tests on said hydrogel;

examples of the formulations of the biocompatible hydrogel;

a description of the methods and the results of chemical, biochemical and medical studies of the novel biocompatible hydrogel;

a description of the ways of correcting cosmetic and functional defects of a human body by means of purposeful injections with the novel biocompatible hydrogel, and information on its practical applications.

To prepare the novel biocompatible hydrogel use was made of the reagents as shown in Table 1.

TABLE 1

REAGENTS FOR PREPARING NOVEL BIOCOMPATIBLE HYDROGEL

| Reagent and empirical formula 1 | Consumption per 100 g of hydrogel, g 2 | Controlables, units and limits 3 |
|---|---|---|
| Akrylamide $C_3H_5NO$ | 3.5–9.0 | Melting point deg. C., 84.5 +/− 0.5 Density, g/cub.cm, 1.122 Basic ingredient, wt. %, not less than 98 |
| Methylene-bis-acrylamide $C_5H_{10}N_2O_2$ | 0.01–1.00 | Melting point deg. C., 184 +/− 1.0 Basic ingredient, wt. %, not less than 96 |
| TMED - tetramethyl-ethylenediamine $C_6H_{16}N_2$ | 0.001–1.00 | Density, g/cub.cm, 0.78 Basic ingredient, wt. %, not less than 98 |
| Ammonium persulfate $(NH_4)_2S_2O_8$ | 0.001–1.00 | Density, g/cub.cm, 1.98 Decomposition point, deg. C., 120 Basic ingredient, wt. %, not less than 98 |
| Bidistilled apyrogenic water | balance | Refraction index, 1.3329 |

Apart from bidistilled water, reagents commercially avaliable under the tradename REANAL (Hungary) were used in the experiments, namely: acrylamide and methylene-bis-acrylamide in the form of white crystals, tetramethylethylenediamine as a white oily liquid and ammonium persulfate in the form of colorless crystals.

Conventionally, the novel biocompatible gel is prepared by the following method:

Under aseptic laboratory conditions, calculated amounts of acrylamide and diluted water solutions of the cross-linking agent (methyl-bis-acrylamide) and initiators of polymerization (ammonuim persulfate and TMED), are introduced into a sterile glass vessel. These reagents are thoroughly stirred, then diluted with water (alternatively with the physiological solution, alternatively other diluted water solution of a physiologically neutral salt, e.g. sodium acetate); the mixture is then filtrated and the filtrate is allowed to stand until the hydrogel of cross-linked polyacrylamide (hereinafter CL PAA) is obtained.

The prepared CL PAA hydrogel is controlled for the following characteristics:

appearance by sight (the hydrogel should be transparent, colorless, free of impurities);

refraction index (to be within the range of 1.334 to 1.350);

pH (to be within the range of 7.0–9.0);

heavy metal contents (to be no less than 0.001% by eight), and sterility.

The invention will be readily understood by reading the following examples.

EXAMPLE 1

Preparation of a low-concentration biocompatible hydrogel 20.3 g of acrylamide, 8.7 ml of a 2% methyl-bis-acrylamide aqueous solution, 7.5 ml of a 1% TMED aqueous solution, and 15 ml of a 4% ammonium persulfate aqueous solution were mixed in a 1 liter capacity glass vessel. Water was then added to obtain a total volume of 580 ml, the mixture was filtered through a glass filter and the filtrate was allowed to stand for at least 20 minutes until 3.5% CL PAA hydrogel was formed.

EXAMPLE 2

Preparation of a high-concentration biocompatible hydrogel 34.2 g of acrylamide, 60 ml of a 1% methyl-bis-acrylamide aqueous solution, 6 ml of a 1% TMED aqueous solution, and 25 ml of a 0.48% ammonium persulfate aqueous solution were mixed in a 1 liter capacity glass vessel. Water was then added to obtain a total volume of 380 ml, the mixture was filtered through a glass filter and the filtrate was allowed to stand for at least 20 minutes until 9% CL PAA hydrogel was formed.

EXAMPLE 3

Preparation of a medium-concentration biocompatible hydrogel 24 g of acrylamide, 50 ml of a 1% methyl-bis-acrylamide aqueous solution, 25 ml of a 1% TMED aqueous solution, and 50 ml of a 1.3% ammonium persulfate aqueous solution were mixed in a 1 liter capacity glass vessel. Water was then added to obtain a total volume of 350 ml, the mixture was filtered through a glass filter and the filtrate was allowed to stand for at least 20 minutes until 5% CL PAA hydrogel was formed.

EXAMPLE 4

Preparation of a low-concentration electroconductive biocompatible hydrogel

The CL PAA hydrogel was prepared as in Example 1, except the physiological solution was used instead of water.

EXAMPLE 5

Preparation of a high-concentration electroconductive biocompatible hydrogel

The CL PAA hydrogel was prepared as in Example 2, except the 9%-sodium acetate aqueous solution was used instead of water.

In experiments, formulations of the CL PAA biocompatible hydrogel (hereinafter BCH) were used as shown in Table 2.

As can be seen in Table 2, the BCH2, BCH3 and BCH4, BCH6, BCH7, BCH8 and BCH9 formulations have the preferred concentrations of CL PAA in the hydrogel, BCH2 and BCH4 being in conformity with the preferable concentration limits of CL PAA in the hydrogel, while all the other formulations reflect intermediate concentrations, and the most preferable ones. In contrast, the BCH1 and BCH5 formulations are representative of the CL PAA concentrations in the hydrogel which are useful in a very limited number of applications.

Laboratory studies of the novel hydrogel were conducted in terms of chemical, biochemical, and medical and biological properties. These studies were not strictly delimited and virtually were based on conventional methods and techniques.

Thus, a dry residue was studied to conventially determine a precise concentration of a substance in a true or colloidal solution.

Then, a dry residue was studied in conformance with the USSR State Standard GOST 15.013-86 "Medical devices" following the technique set-forth in a practical guidance entitled "Methods of analysis of acrylates and methacrylates", KHIMIA publishers, Moscow, 1972 (in Russian).

A precise concentration of CL PAA in the hydrogel is usually determined from a dry residue. This method involves weighing a hydrogel sample and drying thereof to a constant weight (for about 20 hours at 35 deg.C, and residual pressure of 12 to 15 mm Hg followed by a conventional calculation of CL PAA percentage in the hydrogel.

This method was employed for evaluating chemical stability of the novel hydrogel.

To this end, a hydrogel was prepared to contain relatively loosely cross-linked (by introducing 0.25% of methylene-bis-acrylamide by weight of acrylamide) CL PAA of about 5% calculated concentration.

Five samples of such hydrogel of about 20 ml each, were subjected to four sucessive tests as follows:

Test 1. The samples were weighed an dried, at 35 deg.C. and residual pressure 12–15 mm Hg, until a constant weight was reached (for about 20 h.);

Test 2. The samples were weighed, immersed in bidistilled water, boiled for 15 minutes, and dried as above;

Test 3. The samples were weighed, immersed in bidistilled water, bringing up the level to 200 ml in each case, soaked in water for 7 days, water being changed each day, and dried as above;

Test 4. The samples were weighed, soaked in water for 7 days as in Test 3, boiled for 15 minutes as in Test 2 and then dried as above.

TABLE 2

EXAMPLES OF SPECIFIC FORMULATIONS OF NOVEL CL PAA BIOCOMPATIBLE HYDROGEL

| | Formulations and concentrations, % by weight | | | | | | | | |
|---|---|---|---|---|---|---|---|---|---|
| Ingredients | BCH1 | BCH2 | BCH3 | BCH4 | BCH5 | BCH6 | BCH7 | BCH8 | BCH9 |
| CL PAA | 3.0 | 3.5 | 6.0 | 9.0 | 9.5 | 4.0 | 7.0 | 5.0 | 8.0 |
| Na chloride | — | — | — | — | — | — | — | 0.9 | 0.9 |
| Na acetate | — | — | — | — | — | 0.9 | 0.9 | — | — |
| Water | | | | | balance | | | | |

Percentage of the polymer in the gross mass of the hydrogel was calculated by conventional methods for all the samples. The results are shown in Table 3.

TABLE 3

CHEMICAL STABILITY EVALUATION BASED ON DRY RESIDUE OF NOVEL CL PAA BIOCOMPATIBLE HYDROGEL

| Tests | Sample average weight, g, (mean +/- SD) | |
|---|---|---|
|  | Prior to treatment | After treatment |
| 1 | 20.84 +/- 0.96 | 0.983 +/- 0.0048 |
| 2 | 20.15 +/- 0.87 | 0.951 +/- 0.0076 |
| 3 | 20.65 +/- 0.83 | 0.923 +/- 0.0065 |
| 4 | 20.41 +/- 0.63 | 0.913 +/- 0.0095 |

As can be seen from Table 3, even soaking followed by boiling causes no destruction to CL PAA in the hydrogel to indicate that it can be thermally sterilized (whenever, need arises) and features stability though loosely cross-linked.

Next, acrylamide was examined for its capability to migrate into biotissues from stability characteristics of the base of the (CL PAA) hydrogel of the invention in an aqueous medium in conformity with "Guidance on toxicological and hygienic examination of polymeric materials and devices for endoprostheses", Ministry of Public Health of USSR, 1987, p.18-25 (in Russian).

This capability was determined by the HPLC (high performance liquid chromatography) involving detecting UV radiation absorption in the range of 190-210 nm that is typical of the monomer, using a LIQUOCHROM chromatograph (Hungary).

To this end, extracts from the novel hydrogel were obtained by soaking the samples thereof for 14 and 30 days at a temperature of 40 deg.C. and a ratio of 100 ml extractant (bidistilled water) to 1 ml hydrogel. Samples for the HPLC were prepared by drying aliquots of the extracts of 5 ml at room temperature and a residual pressure of 12-15 mm Hg and eluating once a residue at a rate of 0.2 ml/min with a 2 ml 1:1 mixture of water and methanol in a column 150 mm long and 4 mm in diameter filled with the Separon C18 sorbent and by feeding 20 microliters of the eluate into an injector loop.

A minimum of detected concentration of acrylamide by the HPLC was 0.000001 mg/l, whereas its maximum permissible concentration in aqueous extracts from the material from implants was 0.02 mg/l.

Acrylamide was not detected by the HPLC in aqueous extracts from the hydrogel prepared by the method here described to indicate that on the whole both CL PAA and the biocompatible hydrogel of the invention are chemically stable.

In terms of medical and biological properties, the samples of the CL PAA hydrogels prepared by the method here described were tested under laboratory conditions for:

biochemical and hemolitic activity, embriotoxic activity, mutagenic activity, and carcinogenic activity.

Biochemical and hemolitic activity of the CL PAA hydrogels was evaluated from variations of chemical composition of the plasma and blood cell composition in males of albino rats of Wistar line of 300-350 g body weight from test and control groups of 16 animals each.

Prior to experiment, a dose of 5 ml 5% hydrogel of the invention was injected intraperitoneally into each of narcotized rats from the test group.

The rats were fed on a regular basis.

Two weeks thereafter, blood samples were drawn from the rats and were examined for the contents of the ions of Na, K, Ca, Π Cl; urea, blood urea nitrogen and uric acid; creatinine and enzymes (amylase, alkaline phosphatase, alanine- and aspartate-aminotransferase, hereinafter AlAT and AsAT respectively, lactatedehydrogenase, hereinafter LDG, and creatinine phosphokinase) using a KORNING biochemical analyzer (Sweden). In this case, contents of potassium and urea were determined by a LACHEMA bio-test (Czech republic). The results are shown in Table 4.

TABLE 4

EFFECT OF IMPLANTS FROM BIOCOMPATIBLE CL PAA HYDROGEL ON BIOCHEMICAL COMPOSITION OF BLOOD PLASMA IN RATS

| Biochemical characteristics and units therefor | Examination results | |
|---|---|---|
|  | control | test |
| 1 | 2 | 3 |
| Sodium, mmol/l | 151 | 148 |
| Potassium, mmol/l | 8.20 | 6.82 |
| Calcium, mmol/l | 0.97 | 0.90 |
| Chlorides, mmol/l | 97.5 | 102.1 |
| Urea, mmol/l | 4.8 | 4.8 |
| Blood urea nitrogen, mmol/l | 2.2 | 2.2 |
| Creatinine, mmol/l | 0.05 | 0.05 |
| Amylase, mg % | 89.1 | 83.33 |
| Alkaline phosphatase, mmol/l | 84.5 | 55.9 |
| AsAT mmol/l | 133 | 130 |
| AlAt, mmol/l | 41 | 51.7 |
| LDG (total), mmol/l | 217 | 189 |
| Creatinine phosphokinase, units | 5960 | 5685 |
| Uric acid, mmol/l | 0.14 | 0.10 |

As can be seen from Table 4, the main characteristics of the ion exchange demonstrate that there is no manifest damage to the cell membranes. ATPase activity is normal as well.

Stability of characteristics of nitrogen exchange demonstrate normal metabolism including purine exchange and, together with creatinine stability, functional stability of the urogenital system in the presence of CL PAA in a human body.

Normal activity of AlAT and AsAT represents stability of hepatocytes and a proper state of the miocard which, judging from the activity of creatinine phosphokinase being normal, are not subjected to appreciable overloads.

Sufficient activity of alkaline phosphatase is an evidence that there is no inflammation in the endothelium of the biliary ducts.

Also, a blood cell count in the same rats was performed to be shown in Table 5.

TABLE 5

EFFECT OF IMPLANTS FROM BIOCOMPATIBLE CL PAA HYDROGEL ON BLOOD COMPOSITION IN RATS

| Characteristics of blood cells composition and units therefor | Measurement Results | |
|---|---|---|
|  | control | test |
| 1 | 2 | 3 |
| Leukocytes, thsd/mcl | 3.5 + 0.2 | 5.4 |
| Erythrocytes, mln/mcl | 6.86 + 0.43 | 7.02 + 0.31 |

TABLE 5-continued

EFFECT OF IMPLANTS FROM BIOCOMPATIBLE CL PAA HYDROGEL ON BLOOD COMPOSITION IN RATS

| Characteristics of blood cells | Measurement Results | |
| --- | --- | --- |
| composition and units therefor<br>1 | control<br>2 | test<br>3 |
| Hemoglobin, g/l | 125 + 12 | 139 + 9 |
| Hematocrit, % | 35.0 + 1.5 | 36.5 + 1.3 |
| Erythrocyte mean diameter, nm | 51.0 + 0.2 | 52.0 + 1.5 |
| Hemoglobin average content per Erythrocyte, pg | 35.7 + 0.3 | 38.1 + 0.5 |
| Thrombocytes, thsd/mcl | 992 + 12 | 694 + 50 |
| Thrombocyte mean diameter, nm | 8 + 1.5 | 14.25 + 1.6 |

As can be seen from Table 5, leukocytes, in the experiment, unessentially exceed the normal content of 4.5*1000 per cub. mm, while erythrocytes and hemoglobin in erythrocytes indicate normal blood oxigenation. In terms of hematocrit, it can be claimed that a fluid-and-electrolyte balance is approximating normal.

The data available indirectly indicate that biochemical stability and biocompatibility of CL PAA per se, are fairly acceptable.

Embriotoxic activity of the CL PAA hydrogels was determined according to Guidance on experimental and clinical studies of novel drugs, Moscow, Ministry of Public Health of USSR, 1975, p.42–48 and Guidance on toxicological and hygienic examination of polymeric materials and devices for endoprostheses, Moscow, Ministry of Public Health of USSR, 1987 (both documents in Russian).

Three groups of mongrel albino female rats of 180–200 g body weight were used in the experiment, each group containing 16 animals.

The rats in the first group were injected intraperitoneally with 2 ml of the novel 5%-hydrogel to be coupled in a week.

The rats in the second group were also injected intraperitoneally with 2 ml of the novel 5%-hydrogel on the third day of pregnancy.

Pregnant intact rats constituted the third group.

Two rats in the first group showed no pregnancy. 14 rats in the first group and all of 16 rats in the second and third groups gave birth to normal healthy cubs to prove that the novel hydrogel is not embriotoxic.

Mutagenic activity of the CL PAA hydrogels was examined, according to a guidance of the USSR Public Health Ministry "Evaluation of mutagenic activity of chemicals by micronucleous method", Moscow, 1984, 14 pages (in Russian), on reticulocites of the bone marrow from the C3H1-line mice (of both sexes) at the two-month age in two groups of 10 animals each.

Experimental animals were injected with 0.01% by body weight of a 30-day aqueous extract obtained at the temperature of 40 deg.C. and a ratio of 100 ml extractant per 1 g gel from the 9%-CL PAA hydrogel.

In 24 hour period the experimental and intact mice were killed by shifting the spinal marrow. Further, smears of femoral marrow diluted with a serum of fresh non-stabilized human blood of group AB (IV) were conventionally prepared to be Pappenheim stained thereafter.

Reticulocytes with the micronuclei in the smears were counted under the microscope. Variations in the reticulocytes counts in the marrow smears of both the experimental and intact mice in 20 visual fields containing 1000 cells each were not found to exceed 2.3%. It is an evidence that the CL PAA hydrogel does not have any mutagenic effect.

Carcinogenic activity of the CL PAA hydrogel was evaluated by immunodetection of inaccessible tumor-associated antigens.

This type of evaluation involves determination of electrophoretic mobility (hereinafter EPM) of stabilized and tannin-treated erythrocytes which are sensitized to a tumor-associated antigen of rhabdomiosarcoma and, additionally, to an inaccessible embryonal antigen, the latter being an indicator of a tumor progressive growth when the EPM-test is positive. Usually, the EPM-tests are positive, if the electrophoretic mobility of cells-indicators is decreased by 20% or more.

12 non-linear albino male rats of 180–200 g body weight were used in the experiment, constituting a test group and a control group, each containing 6 animals.

The rats in the test group were injected with 4 ml 6% of the CL PAA hydrogel into the femoral muscle under local anesthesia. Then, the rats of both the groups were kept on their usual diet for 18 months. Afterwards, in all the animals blood samples were let from the tail vein, erythrocytes were isolated from the samples and sensitized with the above-mentioned antigens to carry out EPM-tests.

A decrease in the EPM of the sensitized erythrocytes compared with those that were not sensitized was observed as follows:

4.17+/−1.58% for rhabdomiosarcoma antigen and 1.67+/−0.95% for inaccessible embrional antigen in test animals and 1.50+/−0.62 for rhabdomioblastoma antigen and 1.83+/−1.28% for inaccessible embrional antigen in controls.

Therefore, the EPM-test appeared to be negative for the rats of both the groups, which is indicative of the fact that the novel CL PAA hydrogel does not display carcinogenic activity.

More detailed medical and biological examination of the novel CL PAA biocompatible hydrogel applicability in endoprosthetic practice and tamponing was conducted on mongrel male dogs of 25 to 30 kg body weight at the age of three to four years. The dogs were subjected to a test placing of endoprostheses, under sterile conditions, following disinfection of the skin covering of the penis with 10%-iodine tincture and local anesthesia, among which:

6 dogs, subcutaneously, were once injected with 5 ml of the 3.5% CL PAA hydrogel;

also 6 dogs, endofascially, excluding penetration under the tunica albuginea, were injected with the 9%-CL PAA hydrogel into three segments along the penis on opposite sides thereof in the amount of up to 1.5 ml per segment to make the total 8.0 ml, and other 6 dogs, intracavernously, including penetration under the tunica albuginea and mainly into trabecula corporum cavernosum but excluding injury of the urethra, were injected with 6%-CL PAA hydrogel into three segments along the penis on opposite sides thereof in the amount of up to 1.5 ml per segment to make the total 8.0 ml.

The fourth group of three dogs was used as control.

The dogs were killed one by one by an intravenous nembutal injection, among them:

the test animals were killed 1, 7, and 14 days and 1, 3, and 6 months after the CL PAA hydrogel was implanted;

the controls were killed after 1, 3, and 6 months.

Excised pieces of full cross-section slices of the penis, regional lymph nodes, and lungs of the dogs, together with control slices, were fixed in 10 and 6% neutral formaline and in the Carnoy's solution, dehydrated in alcohols of increasing strength and were covered with parafin.

Mounts were stained with hematoxylin and eosin, van Gison-stained with pyrofuchsin, Weigert-stained for elastica, and with toluidine blue at various pH of the staining solution to thereafter detect glycosaminoglycanes by chemical and enzymatic methods.

Glycoproteins and glycogen were detected by the McManus-periodic acid Schiff reaction (hereiafter PAS-reaction), calcium salts were detected by the von Koss method, RNA was detected by the Brachet method (with ribonuclease).

Activity of the following enzymes was studied, namely:

malate dehydrogenase (hereinafter MDG);

succinate dehydrogenase (hereinafter SDG) by the Nachlass method;

lactate dehydrogenase (hereinafter LDG);

glucose-6-phosphate dehydrogenase (hereinafter G-6-PDG), NAD- and NADP-diaphorase by the Hess, by the Scarpelli and by the Pearce methods respectively;

alkaline phosphatase (hereinafter AP) by the Gomori method, and adenosintriphosphatase (hereinafter ATPase) by the Wachstein-Meisel method.

Nervous tissues were impregnated with silver nitrate by the Bielschowsky-Gross method.

Histochemical reactions were conducted and controlled as recommended in the Manual by E.Pearce "HISTOCHEMISTRY" (rus. edition/transl. from the English/2nd Ed.—Moscow, 1962).

The studies revealed that:

A. In the case of subcutaneous injection of the CL PAA hydrogel the following day, a sleeve-like swelling of a soft-elastic consistency with some thinning of the skin was observed at the injection site (one dog developed inconsiderable edema and hyperemia of tissues surrounding the implant with a small focal hemorrhage which had resolved as of the 7th day to be considered as a manipulation injury);

7 days thereafter there were no visually perceptible hemodynamic, alterative, and inflammation reactions. On histological examination, the implant was a large light-blue vacuole surrounded by a thin connective-tissue capsule separating the CL PAA hydrogel and the fascia of the penis and the skin covering. The capsule consisted of one or two layers of young fibroblasts with gentle collagen and elastic fibers to be seen around. Pyroninophilia and enchanced activity of the redox enzymes (SDG, MDG, NAD- and NADP-diaphorases, LDG) and AP are typical of cytoplasma in fibroblasts. An increase in activity of G-6-PDG revealed the activation of pentose-way metabolism. A loose infiltration of leukocytes and macrophages was observed in the layer near the surface of the hydrogel. The capsule had a periphery of granulation tissue of moderate number of newly grown vessels covered with swelled epithelial cells, the lumens of which were locally enlarged and filled with blood formed elements. Proliferating fibroblasts, histiocytes and solitary plasmatic cells were detected in the adventitia of the vessels. In all cases, no giant-cell reaction was observed. Upon staining with toluidine blue, no metachromatic foci were detected at all pH values of the solutions used. A small number of nerve fibers, being impregnated with silver nitrate, showed various changes such as local swelling of axons, loss of their fibrous structure, vacuolization, varicosity, hypo- or hyperimpregnation. At times, accumulation of oxoplasma along the nerve fibers or at their ends, partial unevenness of the myeline membrane and its decomposition into short and long fragments were observed. These changes are typical of the nerve fibers in their compensatory-adaptive restructuring in response to compression from the vacuole on the CL PAA hydrogel;

after 14 days, the macrophage-leukocyte reaction in tissues adjacent the CL PAA hydrogel implant insignificantly increased; a pronounced fibroblastic reaction, including continuous formation of the connective-tissue capsule around the vacuole, was observed, the capsule locally appearing as randomly arranged collagen and elastic fibers having young fibroblasts and newly formed capillaries inbetween, whereas at other locations, as more mature connective tissue consisting of some rows of collagen and elastic fibers arranged side by side as well as proliferating fibroblasts. The RNA-content in cytoplasm and nucleoli increased as well as activity of redox and hydrolytic enzymes. Fibroblast cytoplasm has been enriched in metachromatic granules which are readily detectable with toluidine blue at pH 2.8 to evidence an increase in the synthesis of glycosaminoglycanes. The number of the newly grown vessels sharply decreased in tissues surrounding the capsule, while hystiogenous-type cells producing glycosaminoglycanes and collagen were prevailing in their stead. Giant cells were extremely infrequent. Changes in the nerve fibers were as above;

one month after injection, a mature connective-tissue capsule developed around the vacuole of the CL PAA hydrogel to consist of circularly arranged collagen and elastic fibers with mature fibroblasts inbetween containing a moderate amount of RNA and high-sulfate glycosaminoglycanes detected with toluidine blue at pH 2.8. Activity of redox and hydrolitic enzymes in fibrocytes cytoplasm was normal. A cell reaction that appeared as a loose diffuce infiltration of macrophages and plasmic cells was, at times, observed on the hydrogel surface. The structure of the tissues surrounding the implant was completely normalized and was not different from that of like tissues of the intact animals. Reactive changes in sensitive nerve fibers began to decline and to appear mainly as an irregular enlargement or thinning of the axons and their focal hypo- or hyperimpregnation;

3 months later, some thickening of the CL PAA hydrogel was observed along with an increase in basophilia and a well defined separation of the implant from neighboring tissues by the connective capsule consisting of collagen and elastic fibers and fibrocyte-type cells. Structural and histological changes in the neighboring tissues were not observed, whereas nerve fibers developed their normal shape;

6 months later, the shape and dimensions of the implant remained practically as during the first 24 hours upon injection of the CL PAA hydrogel. Gistologically, the implant appeared as an integral, well encapsulated dark blue vacuole. The capsule consisted of one or two arrays of fibrocytes and orderly arranged collagen and elastic fibers in which no salts of calcium were detected by the von Koss method. The tissues enclosing the implant displayed no reactive, hemodynamical, dystrophic, necrotic, inflammatory and other changes including tissue and cell irregularities. Upon impregnation with silver nitrate, nerve fibers appeared normal.

B. In the case of endofascial injection of the CL PAA hydrogel:

the following day and after 7 days, the penis appeared evenly swelled and showed an increased resiliency. Body temperature of the dogs was normal, skin coloring at the injection sites was as usual, local inflammations were not observed. Histologically, the implants at the injection sites appeared as light blue vacuoles. After seven days, the CL PAA hydrogel vacuoles were observed to be enclosed with thin-walled capsules mainly consisting of one or two layers of young fibroblasts, and gentle connective fibers and some newly formed capillaries surrounding the fibroblast layers, whereas leukocytes and macrophages were observed on the hydrogel surface. The RNA-content in cytoplasm and nucleoli increased as well as activities of SDG, MSG, NAD- and NADP-diaphorases. LDG and G-6-PDG in cytoplasm also increased. The granulation tissue enclosing the capsule had newly formed capillaries with slightly widened and blood-filled lumens and swelled endothelium. Proliferation fibroblasts and some plasmatic cells were found in the adventitia of the blood vessels. Histochemical reactions have confirmed that dystrophic and, moreover, necrobiotic changes were not detected in the fascial tissue enclosing the implants and forced apart by the implants. Thus, upon staining the mounts with toluidine blue solutions at any pH, metachromasy foci, which would suggest of destruction of the CL PAA hydrogel, were not found. Permeability of the vessels remained to be normal since the PAS-positive material was not detected which is stable to amylase and in perivascular spaces as well as in the walls of small and middle-sized vessels, whereas AP and ATP-ase activities in the walls of microcirculatory bed remained to be low. In some cases, the nerve fibres impregnated with silver nitrate and examined by the Spielmeyer method, were observed to be wave- or spiralshaped, and, in other cases, they had swells at the ends. Demyelination sites were rare as was rare local spreading of nerve fibers developing loop-like structures. Infrequent proliferation of hypertrophic Schwann cells was observed. The changes are to be treated as a response of nerve fibers to compression by implants;

after 14 days, the macrophage reaction near the implants was somewhat more intensive but giant cells were not observed. A distinctive fibroblast reaction and the growth of connective tissue capsules around vacuoles were observed; some capsules consisting of randomized collagen and elastic fibers with young fibroblasts therebetween showed a high RNA content in the cytoplasm and enhanced redox activity of enzymes. More mature connective tissue consisting of several arrays of collagen and elastic fibers and fibroblast-type cells was found at other sites. An increased number of histiogenous cells and a decreased number of newly-grown vessels were observed in granulation tissue adjacent the capsules. Endothelium and middle membrane structures, the adventitia of the vessels, and hemodynamic factors did not change while changes of nerve cells were as described in conjunction with the previous term;

in a month time, the implant capsules consisted of cell elements of a fibroblastic series, fibrocytes with a moderately pyroninophilous cytoplasm being predominant. Staining with methylene blue at pH 2.8 showed a moderate number of high-sulfated glycosaminoglycans in fibroblasts. Enzyme activity in the fibrocyte cytoplasm was in accordance with the control. Undersurface layer of the CL PAA hydrogel was to some extent infiltrated by the macrophages and plasmatic cells. There were neither blood-flow disorders, inflammation, degeneration nor necrosis observed in the tissues adjacent the implants. The changes in nerve fibers, mentioned before, were still observed;

3 months after injection, an increase in basophilia of the CL PAA hydrogel was observed. The gel vacuoles were well defined from the fascia by thin connective-tissue capsules of the collagen and elastic fibers with fibrocytes therebetween. Blood vessels were normal. No response of the penis tissues were observed (fascia, as in controls, appeared as circurlarly arranged well defined collagen and elastic fibers without a loss of integrity and without calcipexis at both the micro- and macrolevels, nerve fibers being normal);

after 6 months, the penis as to form and dimensions in the dogs was by visual inspection, similar to that observed on the second-seventh days. Histologically, the implants appeared as integral well-incapsulated darkblue vacuoles. The capsules consisted of one or two arrays of fibrocytes and orderly arranged thin collagen and elastic fibers, and no salts of calcium were found either by the macroscopic or microscopic von Koss method. None of the reactive, hemodynamic, degenerative, necrotic, inflammation or other changes including tissue and cell irregularities were found in the implant-adjacent tissues. Nervous tissues impregnated with silver nitrate, both in the experimental and control animals, were virtually identical. In the regional lymphonodes, intra-trabecular and trabecular spaces of the corpus cavernosum penis, penis veins and in the lungs, the hydrogel particles were not found;

C.In the case of intracavernous injection of the CL PAA hydrogel:

after 1 day and 7 days, staining with hematoxylin and eosin revealed the CL PAA hydrogel appearing as homogenous light-blue vacuoles which, within seven days, were surrounded by thin connective-tissue capsules that caused a shift and slight compression of the trabeculas of the corporum cavernosum penis and tunica albuginea. The capsules consisted of thin, mainly collagen, fibers and one or two arrays of fibroblasts. Connective-tissue of the trabeculas of the corporum cavernosum penis adjacent the capsules were of the usual structure, having clearly defined smooth muscles with a small number of elastic fibers without any traits of degeneration and necrosis on histochemical or histological examination. Minor affluxes of leukocytes and macrophages were observed on the surface of the CL PAA hydrogel implants. Intra-trabecular spaces were filled with minor amounts of blood and the endothelium was slightly swelled. Lesser arteries and veins were moderately filled with blood and having slightly thickened walls (primarily, due to the swelling of endothelium and proliferation of fibroblasts, histiocytes and plasmatic cells in the adventitial membranes). Capsules were observed to be surrounded by granulation tissue consisting of a small number of the thin-walled newly-grown vessels and different cells, mainly of a histiogenous origin such as fibroblasts, histiocytes. Some nerve fibers, when impregnated and examined by Spielmeyer method, showed changes in axon, the myelin membrane, and Schwann cells. There were no giant-cells observed as a result of the resolution of foreign matter. There were observed twisting, local swelling and irregular thickenings in nervous tissues as well as varicosity and a loss of fibrous structure in axons, spherical and club-shaped enlargements at their ends, and lokal demielinization. Reactive proliferation of Schwann cells, some of which hypertrophied, was found;

after 14 days, the leukocyte and macrophage reaction around the CL PAA hydrogel implants became somewhat more intensive but the giant cells capable of resolving foreign matter were, as mentioned before, not found. The connective-tissue capsules around the implants were, in some cases, slightly porous and consisted of randomly scattered collagen and elastic fibers and young fibroblasts, and some of them appeared more mature and constisted mainly of parallel collagen fibers including elastic fibers and fibroblastic elements. Perifocal granulation tissue was consisting of a small number of flatened newly-grown vessels and fibroblasts containing a moderate amount of RNA and granules of highly-sulfated glycosaminoglycans. Changes in nervous tissues occured as a local swelling of axons, loss of fibrous structure in them, vacuolization, varicosity, hypo- and hyperimpregnation and, occasionally, in local accumulation of the oxoplasm, either along the nerve fibers or at their ends, a partial roughness of the myeline membrane and its disintegration into short and long fragments, what should be considered as a compensatory-adaptive response to compression. In the regional lymphonodes, intertrabecular spaces of corporum cavernosum, the veins of the penis and in the lungs, CL PAA hydrogel particles were not detected;

after in a month, the CL PAA hydrogel implants were surrounded by thin mature connective-tissue capsules consisting of circlularly arranged collagen and elastic fibers with mature fibroblastic elements found between their arrays. Inconsiderable diffusive infiltration of macrophages and plasmatic cells was observed in the layers of the implants adjacent their surface. Connective-tissue trabeculas of the corporum cavernosum were not structurally differrent from the controls and were covered with the normal endothelium. A small amount of blood could be found in the intertrabecular spaces. The walls of the corporum cavernosum veins and arteries showed no visible structural changes. Reactive changes in nerve fibers, compared with the previous period, were less distinct and appeared mainly as irregular thickenings or thinnings in axons and local hypo- or hyperimpregnation;

after 3 months, the hydrogel was getting thicker and became basophilic. The implants were separated from adjacent tissues with thin-walled capsules of parallel collagen and elastic fibers with a small number of fibrocytes between them. Cell elements were not observed on the surface of the implants. Adjacent tissues with blood vessels were of the usual structure. Glycosaminoglycans in the ground interstitial substance, fibrous formations and cell elements of connective tissue were virtually identical to those in the control. Changes in nerve fibers were not observed;

after 6 months, the penis in dogs was of the shape and dimensions by visual observation, similar to those observed on the second-seventh days. Histologically, the implants appeared as integral well-incapsulated dark-blue vacuoles. The capsules consisted of one or two arrays of fibrocytes and regularly arranged thin collagen and elastic fibers, and no salts of calcium were found either by the macroscopical or microscopical von Koss method. There were observed no reactive, hemodynamic, degenerative, necrotic, inflammatory and other changes, including tissue and cell irregularities, in the tissue adjacent the implant. Upon impregnation with silver nitrate, nerve fibers appeared virtually identic in the experimental and control animals. In the regional lymphonodes, in inter-trabecular spaces of the corporum cavernosum and the veins of the penis as well as in the lungs, the CL PAA hydrogel particles were not found.

Similar morphologic data were obtained by clinical experiment. Used as a test material was a bioptic sample of hypodermic cellular tissue taken in a healthy male volunteer, age 45, who, 6 years prior to biopsy, was intradermally injected with 10 ml of the novel hydrogel at 8% concentration CL PAA.

The bioptic sample was fixed in 10% formaline, dehydrated in alcohols of increasing strength and embedded in parafin. Mounts were stained with hematoxylin and eosin; the collagen fibers were determined by the van Gison method and the elastic fibers with resorcin-fuchsin by the Weigert method; glycosaminoglycanes were determined with toluidine blue solutions at various pH values applying the required chemical and enzymatic control; glycoproteide and glycogen concentrations were determined by means of the PAS-reaction by the McManus method.

Macroscopically, the bioptic sample was oval in shape, soft elastic, light-pink in color without any visible changes which would distinguish it from adjacent tissues.

On microscopic examination, all preparations showed the CL PAA hydrogel stained with hematoxylin and eosin to acquire blue color of various degree of intensity. The hydrogel implant was threaded throughout with well vascularized gentle connective tissue mainly consisting of orderly-arranged collagen and elastic fibers and the ground substance which included an insignificant number of cell elements (as a rule, such as inactive fibroblasts, because, on staining with toluidine blue at pH 2.8, no traits of metachromasy evidenced by glycosaminoglycans were detected in the cytoplasm of these fibroblasts, and such as solitary mononuclears-macrophages).

This connective-tissue had the vessels located as groups and having walls of irregular thickness with the flatened endothelium.

Signs of acute and chronic inflammation, such as polymorphonuclear leukocytes, epithelioid cells, giant cells capable of resolving foreign matter and both lymph and histiocy infiltrates, were entirel absent, as absent were signs of allergic reactions, such as lymphocytes, macrophages and histiocytes as well as signs of hemodynamic disorders such as plethora of the vessels, pre-stasis, hemostasis, thrombosis, and malignization, e.g. cell or tissue irregularities and cell proliferation. Calcium salts were not detected in the mounts, either macro- or microscopically. Alterative, i.e. dystrophic or necrotic, changes were not found.

A fibrous capsule surrounding the implant was not observed.

The basic method of correcting cosmetic or functional defects in a human body by using the novel CL PAA biocompatible hydrogel consists in the following:

based on anamnesis, examination and, if required, laboratory studies generally acceptable for patients to be surgically treated (particularly for individual response to antibiotics), a tentative conclusion is drawn up as follows:

first, the organ to be treated either as to its form and dimensions or functional efficacy, is defined, and second, an amount, tactics and a form (outpatient or patient) of the future treatment are planned;

prior to injection of the novel hydrogel, anesthesia (as a rule, local infiltration) is induced;

Sterile CL PAA hydrogel, additionally saturated with antibacterial preparations, is syringed at a low rate (usually, in two or three stages) into the site to be treated at a temperature approximating normal body heat (36 deg.–37 deg.C.).

This method is the most applicable in mammaplasty (preferably, in the case of aplasia and hypomastia) and alloplasty, in the case of impotency manifested as poor erection due to age or prior injuries.

Thus, in mammoplasty, the CL PAA hydrogel having a preferable concentration within the range of 3.5–6.0% and the most preferable concentration within the range of 5.0–6.0%, is injected retromammarily, intracapsularly and/ or subfascially, in two or three stages depending on the individual anatomic mamma pecularities, usually in the amount of 40–160 ml (but not exceeding 200 ml) per mamma per stage.

In phalloplasty, the CL PAA hydrogel having a preferable concentration within the range of 4.5–6.0% and the most preferable concentration of 5.0%, is, as a rule, intracavernously injected into three trabecular segments along each side of the penis. A total amount of the CL PAA hydrogel required for one phalloplastic operation is preferably within the range of 40 to 60 ml. The specific amount of the hydrogel to be injected is calculated from the criteria of acceptable volume and resilience of the penis, possible compression of the urethra excluded.

The novel biocompatible hydrogel was clinically tested.

Specifically, it was applied for cosmetic correction of facial congenital defects and in mammoplasty in cases of aplasia and hypomastia in women.

Patient records, by way of example, are presented as follows:

(1) Patient M. (case record No.15D), b. 1965.

Diagnosis: Congenital right-side mandibulo-neuromuscular craniofacial microsomia.

Treatment (general anesthesia: intravenous and NLA):

the first stage (November, 1993)—two injections of 10 ml of the 3.5% CL PAA hydrogel intramuscularly;

the second stage (June, 1994)—the injections and the hydrogel (15 ml) as above.

Improvement is of record: the right and left sides of the face appeared symmetrical.

(2) Patient L. (case record No. 12), b. 1967, parous.

Diagnosis: Symmetrical mamma aplasia.

Treatment in three stages (local anesthesia: 0.5% novocain solution, 80 ml):

the first stage (January, 1991)—intramuscular, retromammar, and subcapsular injections of 140 ml of the 6.0% CL PAA hydrogel into both mammas;

the second stage (March, 1991)—the injections and the hydrogel (40 ml) as above;

the third stage (May, 1991)—the injections and the hydrogel (60 ml) as above.

Improvement is of record: the patient's mammas, in shape and dimensions, are consistent with her physique; their resilience is similar to natural soft tissues.

(3) Patient N. (case record No.78), b.1969, nonparous.

Diagnosis: Symmetrical hypomastia.

Treatment (local anesthesia: 0.5% novocain solution, 80 ml):

the first stage (February, 1993)—intramuscular, retromammar, and subcapsular injections of 130 ml of the 6.0% CL PAA hydrogel into both mammas;

the second stage (March, 1993)—the injections and the hydrogel (100 ml) as above.

Improvement is of record as in the above case.

(4) Patient K. (case record No.17L), b. 1967, parous.

Diagnosis: Symmetrical hypomastia.

Treatment (local anesthesia: 0.5% novocain solution, 80 ml):

the first stage (January, 1994)—intramuscular, retromammar, and subcapsular injections of 130 ml of the 6.0% CL PAA hydrogel into both mammas;

the second stage (July, 1994)—the injections and the hydrogel (60 ml) as above.

Improvement is of record as in the above case.

The effect of the treatment, in this case, was additionally evaluated from the data obtained by computerized axial tomography of the chest on a SIEMENS "SONATRON CR" tomograph (Germany) by scanning each 8 mm deep section of the treated mamma in a supine position. Two tomograms of the many that were taken are shown here as follows.

Figure 1:
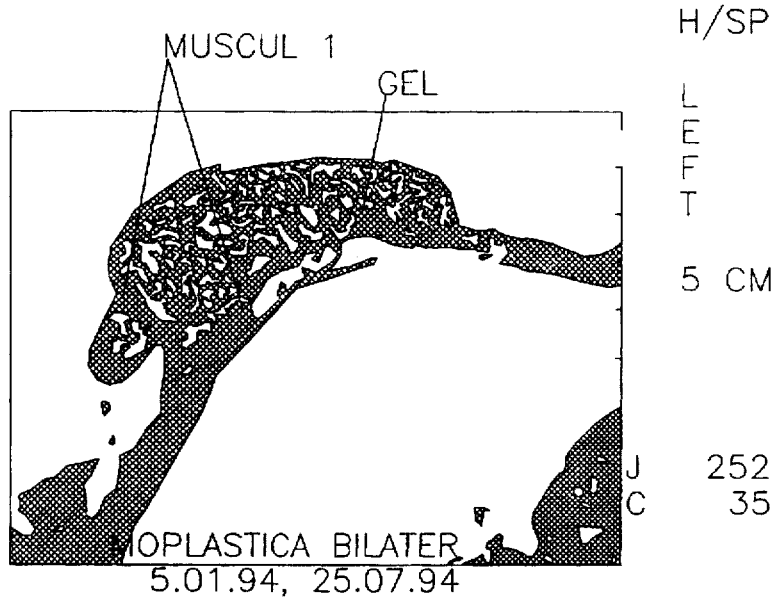
FIG. 1 illustrates the left mamma after treatment for malformation and size correction.
Figure 2:
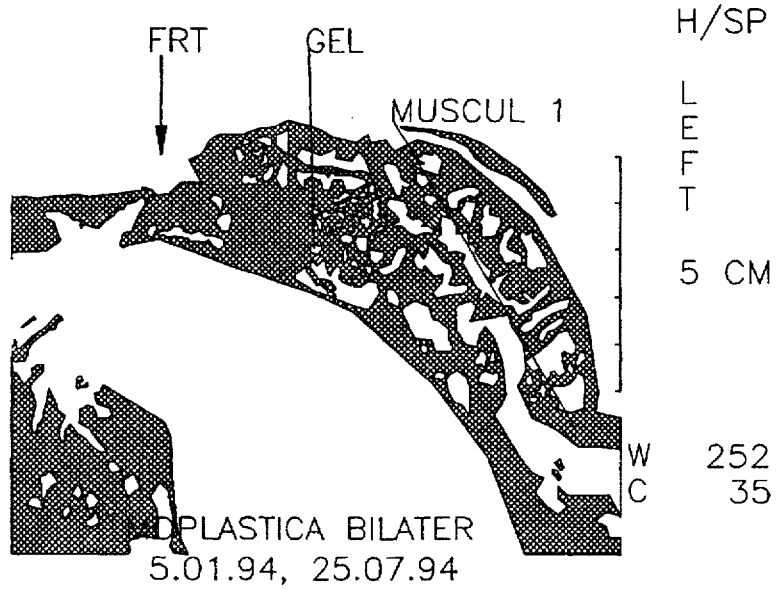
FIG. 2 illustrates similar form and size correction of the right mamma.

As can be seen in the illustrations, both the mammas, as a result of the treatment, are found to have a regular topography and form. Skin thickness does not exceed 2.0 mm, the teats and areolas are normal (neither deformed nor drawn in). Hypoplastic glandular tissue of both the mammas is ventrally shifted by the CL PAA hydrogel (differring in density compared to that of the tissue) injected into the retromammary space (density of glandular tissue is +3.0 to +4.0, density of the hydrogel is +4.6 to +7.2, and density of hypodermic adipose cellular tissue is −73 to −95 units Hu).

Glandula mammaria dimensions after treatment are as follows:

transversal of 7.4 cm dextra et 8.0 cm sinistra;

anteroposterior about 5.0 cm dextra et sinistra.

Regional lymphonodes are not enlarged, osseous tissues of breast bones and ribs are normally structured.

Laboratory, experimental and clinical data allow to conclude that the novel CL PAA hydrogel is chemically and bioligically stable, inert, biocompatible, and perfectly suitable for implantation as endoprostheses, for tamponing of caverns and for formation of intratissue storage sites for prolonged-action medicinal preparations.

The novel biocompatible hydrogel was tested as a medium for long-term cardio- and encephalography on samples having the CL PAA concentration within the range of 4.0–8.0% and prepared on the 0.9% aqueous solution of sodium chloride and sodium acetate.

The test included the following:

measurement of electrical resistivity of the hydrogel arranged as 1 mm layer between disk-type electrographic electrodes (type EKMK-6) 9 mm in diameter and 3 mm in thickness, with a tin-, copper- or aluminum-plated contact surface, measurement of the electrical resistivity as to its 24-hour stability, and determination of abilities to bear prolonged (1, 7, and 15 day observation) applications to a forearm skin area near the elbow of medical staff volunteers including two men and two women.

The electrical resistivity was from 8.0 to 9.0 kOhm/cm of the BCH6 and BCH7 samples and from 10.0 to 20.0 kOhm/cm of the BCH8 and BCH9 samples; and it remained unchanged for each sample during a 24-hour period, measurements being repeated every three hours. By comparison, the electrode paste commercially available from SIEMENS AG has an electrical resistivity of about 8.0 kOhm/cm.

In all tests, the polarizability of tin-plated electrodes was about 450 mV, of copper-plated electrodes was 150 mV, and of aluminum-plated electrodes was about 700 mV. In measuring the electrical resistivity no parasitic polarization was felt.

On visual observation, none of the skin application sites, during the above mentioned periods, showed visible irritations (reddening or pruritus) and, what is more, skin injuries (maceration). On day 15 in one case, the skin around the plaster covering the hydrogel application turned pink in one of the women-volunteers.

Spontaneous flow of the CL PAA hydrogel having viscosity of 10–11 poise, out of the space between the horizontally arranged measuring electrodes or from underneath the plasters, was not observed.

These data indicated that the novel CL PAA hydrogel is applicable as an immersion medium for monitoring the electrophysiologic parameters of a human organism and for electrophoretic drug injection through the skin.

I claim:

1. Biocompatible hydrogel for placing endoprostheses by injection, containing cross-linked polyacrylamide produced by radical polymerization and pyrogen-free water, said cross-linked polyacrylamide constituting from 3.5 to 6.0% by weight based on the total weight of the hydrogel.

* * * * *